(12) United States Patent
Livengood et al.

(10) Patent No.: US 8,191,909 B2
(45) Date of Patent: Jun. 5, 2012

(54) MODULAR PATIENT SUPPORT SYSTEM

(75) Inventors: Joseph C. Livengood, Fort Collins, CO (US); Heather N. Bean, Fort Collins, CO (US); Amy L. Livengood, Fort Collins, CO (US); Philip A. Livengood, Fort Collins, CO (US); Joseph D. LoBue, Nunn, CO (US); Barry T. Phillips, Fort Collins, CO (US)

(73) Assignee: Livengood Engineering, Inc., Fort Collins, CO (US)

( * ) Notice: Subject to any disclaimer, the term of this patent is extended or adjusted under 35 U.S.C. 154(b) by 811 days.

(21) Appl. No.: 12/244,623

(22) Filed: Oct. 2, 2008

(65) Prior Publication Data

US 2009/0085317 A1 Apr. 2, 2009

Related U.S. Application Data

(63) Continuation-in-part of application No. 11/329,860, filed on Jan. 10, 2006, now Pat. No. 7,562,883.

(60) Provisional application No. 60/976,965, filed on Oct. 2, 2007, provisional application No. 60/642,836, filed on Jan. 10, 2005.

(51) Int. Cl.
*B62B 5/04* (2006.01)
(52) U.S. Cl. ............. 280/47.34; 188/19; 280/87.01
(58) Field of Classification Search .......... 280/87.01, 280/79.11, 79.3, 47.34, 47.35, 33.994, 43.17, 280/43.22, 43.24; 188/2 D, 19; 135/67
See application file for complete search history.

(56) References Cited

U.S. PATENT DOCUMENTS

| 1,793,353 | A | | 9/1928 | Benson |
|---|---|---|---|---|
| 2,712,366 | A | | 7/1951 | Skupas |
| 2,783,055 | A | | 2/1957 | Michaud |
| 3,441,974 | A | | 5/1969 | Dean |
| 3,563,563 | A | * | 2/1971 | Radovic ............ 280/79.11 |
| 3,831,960 | A | | 8/1974 | Walton |

(Continued)

FOREIGN PATENT DOCUMENTS

CA 2149336 8/1994

(Continued)

OTHER PUBLICATIONS

International Search Report for International (PCT) Patent Application No. PCT/US08/078609, mailed Dec. 3, 2008, pp. 1-4.

(Continued)

*Primary Examiner* — Frank Vanaman
(74) *Attorney, Agent, or Firm* — Sheridan Ross P.C.

(57) ABSTRACT

A patient support platform or mobile support cart is provided. The mobile support cart includes a transmission system that allows the patient and/or medical staff member to choose a stop, walk or roll mode. In the stop mode, the castor wheels are prevented from rolling across the floor by a braking mechanism. In the walking mode, the transmission causes a tracking wheel to engage the floor for providing tracked or guided motion to the mobile support cart. In a roll mode, the tracking wheel is raised and is disengaged from the floor, and the castor wheels are free to rotate. The platform is capable of supporting devices that may be attached or associated with a patient throughout their stay at a healthcare facility. The braking mechanism can include a cable and an associated brake arm, with the cable positioned to allow braking without inhibiting the ability of the castor wheel to swivel with respect to a castor mounting plate.

14 Claims, 7 Drawing Sheets

U.S. PATENT DOCUMENTS

| | | | | |
|---|---|---|---|---|
| 3,951,426 | A | 4/1976 | Shaffer et al. | |
| 4,093,900 | A | 6/1978 | Plunkett | |
| 4,248,445 | A * | 2/1981 | Vassar | 280/79.11 |
| 4,302,025 | A | 11/1981 | Waddell et al. | |
| 4,385,414 | A | 5/1983 | Damico | |
| 4,511,157 | A | 4/1985 | Wilt | |
| 4,515,235 | A | 5/1985 | Yamamoto et al. | |
| 4,832,294 | A | 5/1989 | Eidem | |
| 4,970,900 | A | 11/1990 | Shepherd et al. | |
| 4,998,320 | A | 3/1991 | Lange | |
| 5,083,625 | A | 1/1992 | Bleicher | |
| 5,083,807 | A | 1/1992 | Bobb et al. | |
| 5,094,418 | A | 3/1992 | Metzler et al. | |
| 5,112,019 | A | 5/1992 | Metzler et al. | |
| 5,115,539 | A | 5/1992 | Lee | |
| 5,117,521 | A | 6/1992 | Foster et al. | |
| 5,118,127 | A | 6/1992 | Partington | |
| 5,128,117 | A | 7/1992 | Olry et al. | |
| 5,205,381 | A * | 4/1993 | Mehmen | 188/19 |
| 5,261,682 | A | 11/1993 | Chuang | |
| 5,306,109 | A | 4/1994 | Kreuzer et al. | |
| 5,319,816 | A | 6/1994 | Ruehl | |
| 5,337,992 | A | 8/1994 | Pryor et al. | |
| 5,344,169 | A | 9/1994 | Pryor et al. | |
| 5,358,205 | A | 10/1994 | Starkey et al. | |
| 5,377,372 | A | 1/1995 | Rudolf et al. | |
| 5,411,044 | A | 5/1995 | Andolfi | |
| 5,476,432 | A * | 12/1995 | Dickens | 482/67 |
| 5,503,416 | A * | 4/1996 | Aoki et al. | 280/79.11 |
| 5,509,680 | A | 4/1996 | Scharf et al. | |
| 5,551,105 | A | 9/1996 | Short | |
| 5,699,988 | A | 12/1997 | Boettger et al. | |
| 5,704,577 | A | 1/1998 | Gordon | |
| 5,735,367 | A | 4/1998 | Brubaker | |
| 5,774,936 | A | 7/1998 | Vetter | |
| 5,857,685 | A | 1/1999 | Phillips et al. | |
| 5,898,961 | A | 5/1999 | Ambach et al. | |
| 6,000,486 | A | 12/1999 | Romick et al. | |
| 6,073,285 | A | 6/2000 | Ambach et al. | |
| 6,098,732 | A | 8/2000 | Romick et al. | |
| 6,099,002 | A | 8/2000 | Uchiyama | |
| 6,123,346 | A | 9/2000 | Baldwin | |
| 6,179,260 | B1 | 1/2001 | Ohanian | |
| D438,952 | S | 3/2001 | Cimino et al. | |
| 6,231,016 | B1 | 5/2001 | Slone | |
| D447,567 | S | 9/2001 | Murphy et al. | |
| 6,286,183 | B1 | 9/2001 | Stickel et al. | |
| 6,315,308 | B1 | 11/2001 | Konopka | |
| 6,360,389 | B1 * | 3/2002 | Gallant et al. | 5/658 |
| 6,375,133 | B1 | 4/2002 | Morrow | |
| 6,394,470 | B1 | 5/2002 | Shirai | |
| D467,001 | S | 12/2002 | Buczek et al. | |
| 6,494,469 | B1 | 12/2002 | Hara et al. | |
| D477,083 | S | 7/2003 | Bromley | |
| 6,602,227 | B1 | 8/2003 | Cimino et al. | |
| 6,626,445 | B2 | 9/2003 | Murphy et al. | |
| 6,708,991 | B1 | 3/2004 | Ortlieb | |
| 6,725,483 | B2 * | 4/2004 | Gallant et al. | 5/658 |
| 6,865,775 | B2 | 3/2005 | Ganance | |
| D503,981 | S | 4/2005 | Fischer et al. | |
| 6,874,800 | B2 | 4/2005 | George | |
| 6,971,656 | B2 | 12/2005 | Lin | |
| D518,267 | S | 3/2006 | Arceta | |
| 7,182,178 | B2 * | 2/2007 | Chung | 188/1.12 |
| 7,182,350 | B1 | 2/2007 | Liao | |
| 7,243,666 | B2 * | 7/2007 | Carroll | 135/67 |
| D598,107 | S | 8/2009 | West et al. | |
| 2002/0068914 | A1 | 6/2002 | Ikeda | |
| 2002/0096608 | A1 | 7/2002 | Cedarberg | |
| 2004/0036386 | A1 | 2/2004 | Olivera | |
| 2004/0046487 | A1 | 3/2004 | Olivera et al. | |
| 2004/0059303 | A1 | 3/2004 | Anderson et al. | |
| 2004/0105733 | A1 | 6/2004 | Hewitt | |
| 2004/0262867 | A1 | 12/2004 | Arceta et al. | |
| 2005/0023787 | A1 | 2/2005 | Haynes | |
| 2006/0082088 | A1 | 4/2006 | Webster et al. | |
| 2006/0163829 | A1 | 7/2006 | Livengood et al. | |
| 2007/0107761 | A1 | 5/2007 | Kovachi et al. | |

FOREIGN PATENT DOCUMENTS

| | | |
|---|---|---|
| GB | 2312055 | 8/1996 |
| WO | WO 00/09061 | 2/2000 |
| WO | WO 02/15837 | 2/2002 |
| WO | WO 02/24252 | 3/2002 |
| WO | WO 03/016719 | 2/2003 |
| WO | WO 03/094817 | 11/2003 |

OTHER PUBLICATIONS

Written Opinion for International (PCT) Patent Application No. PCT/US08/078609, mailed Dec. 3, 2008, pp. 1-5.

Restriction Requirement for U.S. Appl. No. 29/325,581, mailed Nov. 10, 2009, pp. 1-4.

Official Action for U.S. Appl. No. 29/325,581, mailed Dec. 10, 2009, pp. 1-6.

Notice of Allowance for U.S. Appl. No. 29/325,581 mailed Apr. 23, 2010, pp. 1-7.

Examiner's Report for Canadian Design Patent Application No. 130231, mailed Nov. 20, 2009, pp. 1-3.

Notice of Allowance for U.S. Appl. No. 29/350,539, mailed Apr. 26, 2010, pp. 1-7.

Notice of Allowance and Fees Due for U.S. Appl. No. 11/329,860, mailed May 11, 2009, pp. 1-5.

International Preliminary Report on Patentability (PCT) Patent Application No. PCT/US2006/000893, mailed May 14, 2009.

International Preliminary Report on Patentability for International (PCT) Patent Application No. PCT/US08/078609, mailed Apr. 15, 2010, pp. 1-7.

Examiner's Report for Canadian Design Patent Application No. 134450, mailed Apr. 29, 2010, pp. 1-4.

Examiner's Report for Canadian Design Patent Application No. 130231, mailed Apr. 29, 2010, pp. 1-3.

Author Unknown, "Computer Carts; StyleView™ Cart with CF™", ERGOTRON, as early as Oct. 10, 2004, pp. 1-2, available at http://www.ergotron.com/3_products/carts/sview/default.asp.

International Search Report for International (PCT) Patent Application No. PCT/US06/00893, mailed Aug. 8, 2008.

Written Opinion for International (PCT) Patent Application No. PCT/US06/00893, mailed Aug. 8, 2008.

Official Action for U.S. Appl. No. 11/329,860, mailed Jun. 20, 2008, pp. 1-12.

* cited by examiner

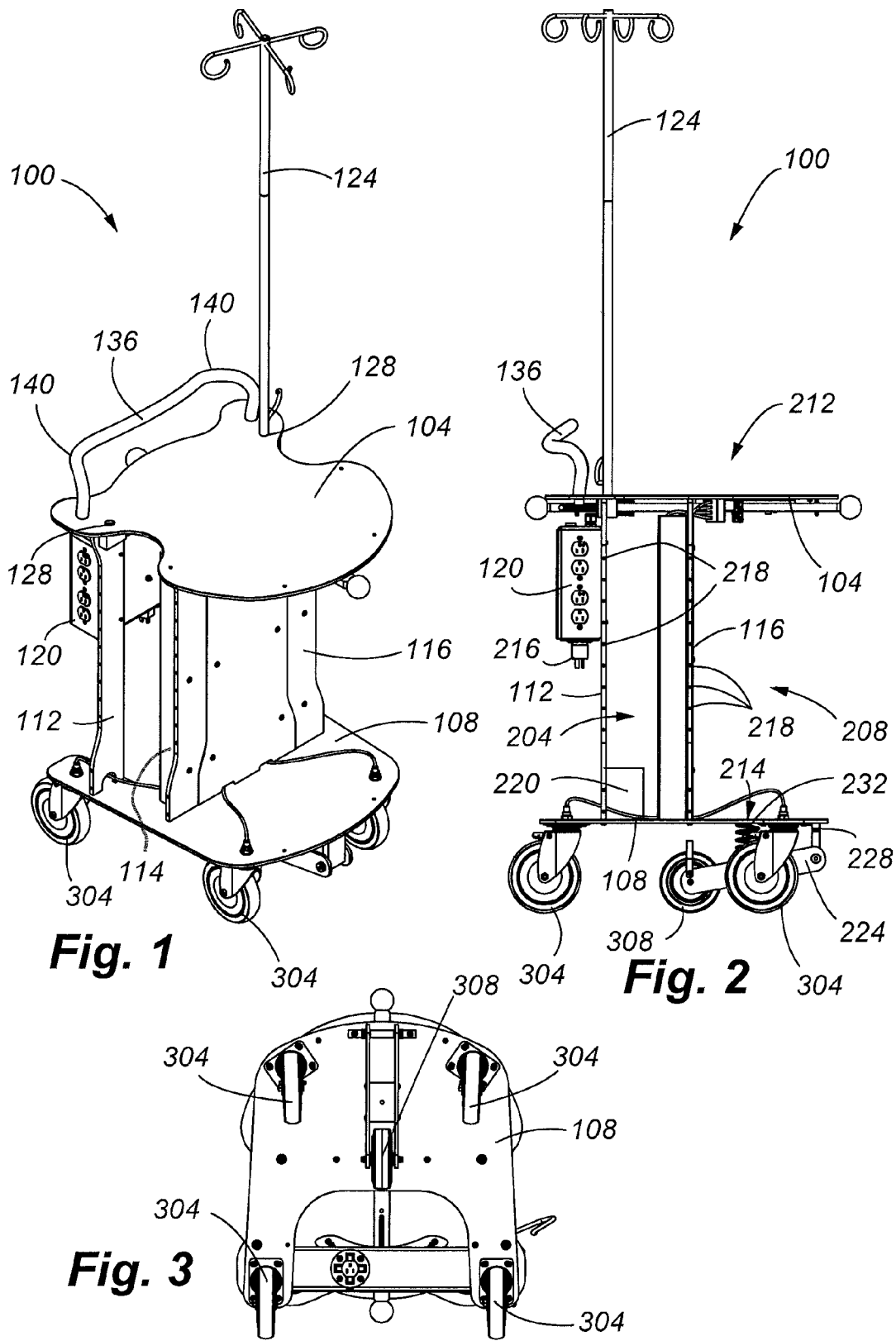

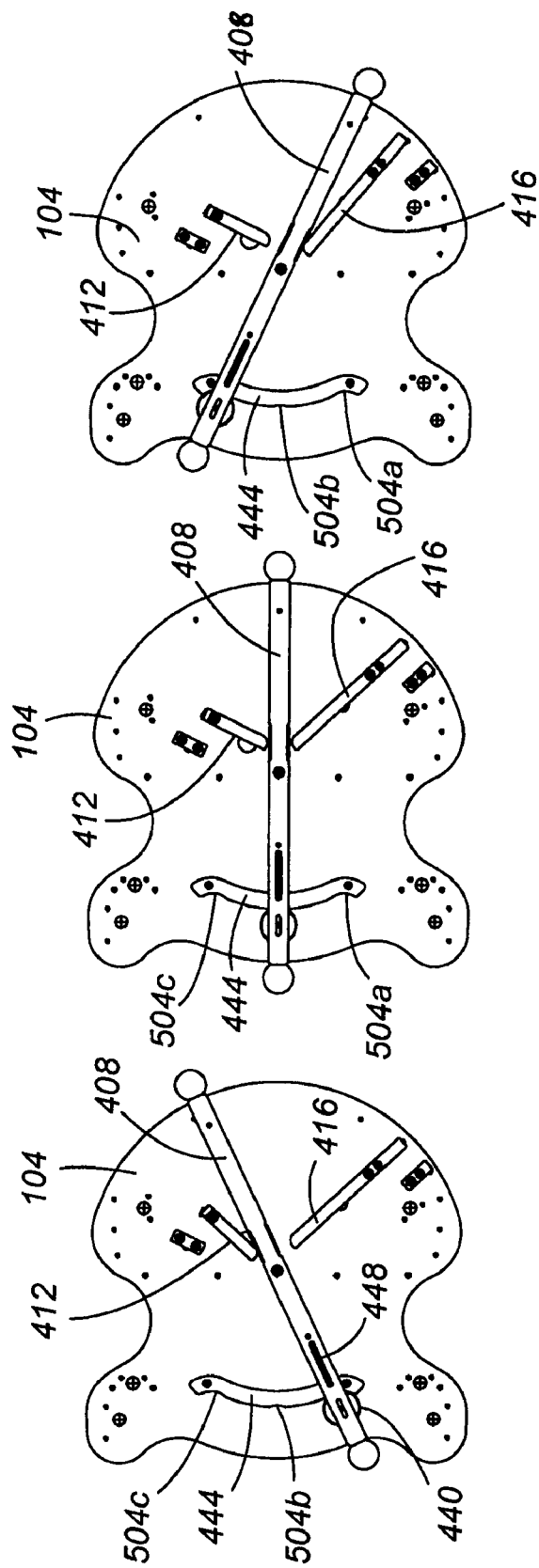

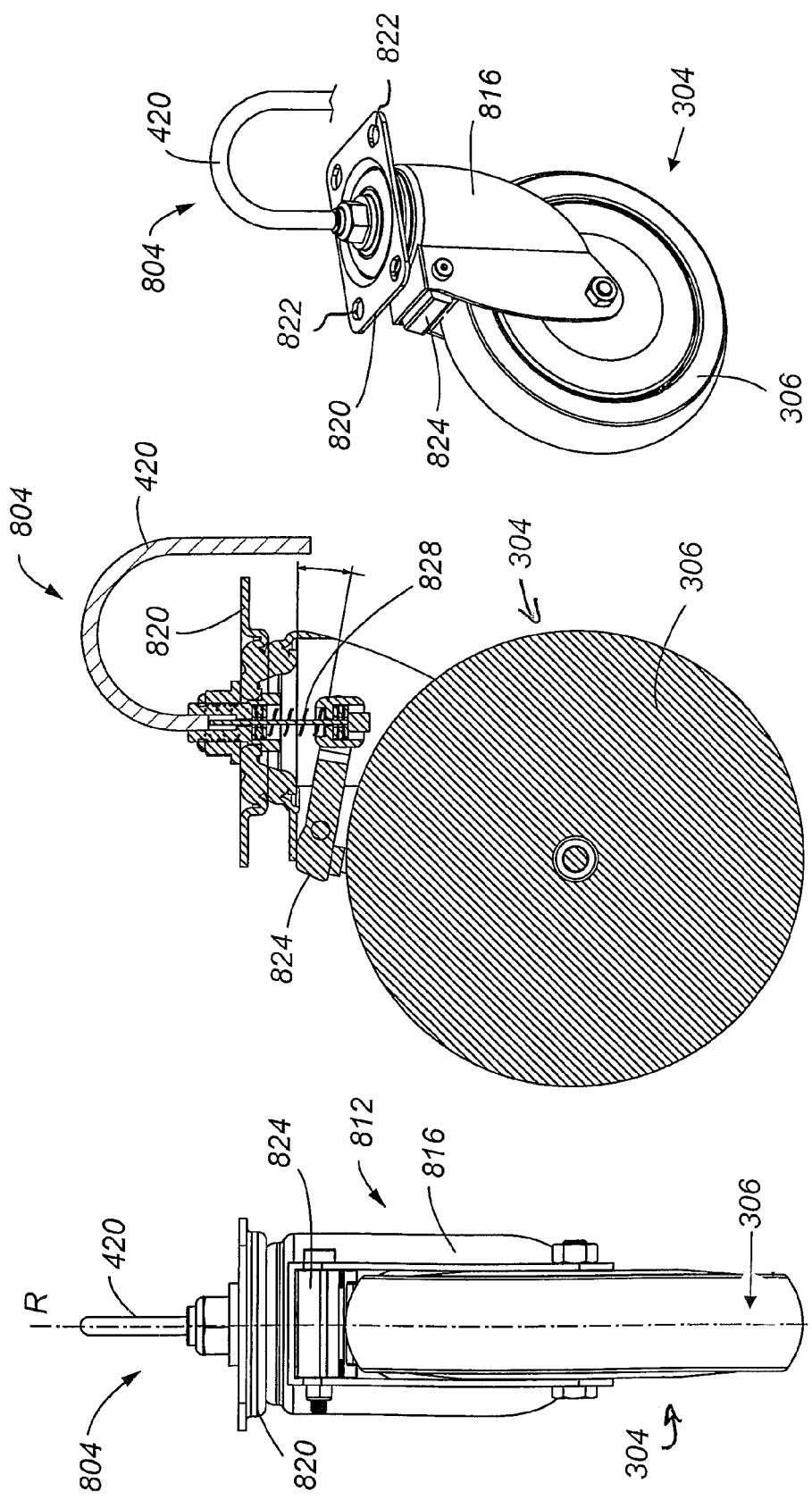

MODULAR PATIENT SUPPORT SYSTEM

CROSS-REFERENCE TO RELATED APPLICATIONS

The present application claims the benefit of U.S. Provisional Patent Application Ser. No. 60/976,965 filed Oct. 2, 2007. The present application is also a continuation-in-part application of U.S. patent application Ser. No. 11/329,860 filed Jan. 10, 2006, which claims the benefit of U.S. Provisional Patent Application Ser. No. 60/642,836 filed Jan. 10, 2005. The entire content of the above applications are incorporated herein by reference in their entirety.

FIELD

The present invention is generally directed to support platforms and/or carts that provide enhanced patient mobility.

BACKGROUND

Current practice for patients in a healthcare facility involves having multiple unrelated treatment, maintenance and/or monitoring devices that are attached to the patient. These include intravenous fluids and drugs, drainage catheters, suction catheters, leg compression stockings and vital sign monitoring devices. Such devices often create a hazard for the patient both directly and indirectly. The myriad of devices may become entangled and inadvertently removed if not adequately accounted for by the patient or caregiver. This may require an invasive intervention, including surgery, in order to replace the removed device.

The number of devices generally associated with the patient require the patient to have the physical and mental ability to manage organizing or carrying the devices to ambulate even as far as the bathroom. Since patients are debilitated by the nature of their illness and medications, two staff persons are frequently required to help the patient move even short distances. One staff member must assist the patient, providing physical support, while the other manages the attached devices. The patients thus do not get out of bed and ambulate as often since the staff of the typical health facility is not able to provide this kind of support readily to all of the patients at all times.

The resulting immobility increases the patient's risk for deep venous thrombosis, pulmonary embolus and pneumonia. Additionally, mobility improves gut motility and decreases the time a patient must wait before obtaining enteral nutrition and ultimately discharge from the healthcare facility. Patients that require prolonged hospital stays or admission to skilled-nursing facilities for non-medical indications related to mobility and personnel support may be able to be discharged home sooner with a device that provides the same type of care. The cost to the healthcare system may be reduced by decreasing the stays in expensive healthcare facilities and decreasing complications that are costly both in patient morbidity and monetary value.

The patient-care staff is also at risk for injury, as they must provide physical support to the debilitated patient. Back injuries are frequent in healthcare staff as a result of the physical nature of assistance provided. Allowing the patient to rely on an ambulatory assist device will help the patient-care staff as well by keeping them out of harm's way.

Current poles that provide an intravenous ("IV") fluid and/or liquid medication delivery source are often times taken with patients when the patient moves around, such as when a patient walks in a hospital hallway. The patient typically places at least one hand on the IV pole to move the IV pole while walking. However, typical IV poles are approximately 6 to 7 feet tall, and are often unstable for providing weight support to a patient, particularly when one or more substantially full IV bags are positioned near the top of the pole. As a result, a patient is at risk of further injury by falling if the IV pole tips and/or falls over. In addition, in order to prevent tipping, conventional IV poles have widely spread wheels, which require a large amount of floor space. IV poles are completely unable to manage uneven terrain as is found outside the confines of the patient care facility, and as may be found at home or in the field for disasters or military operations.

In addition to being relatively unstable, current IV poles do not provide for the additional needs of a patient that is moving about. For example, IV poles do not include an oxygen source for assisting the patient with breathing. Current IV poles also do not include various pumps or suction devices that may be necessary for continuous operation to provide proper medical treatment to the patient. In addition, vitals monitoring equipment and communication devices are typically not present on a standard IV pole. Furthermore, even if an IV pole is adapted to include a monitoring device or pump, the IV pole tends to become even more unstable because the resulting added weight of the device typically is positioned relatively high along the pole.

In connection with patients that require assistance walking, various "walker" devices are available. A typical walker includes handrails interconnected to a stable base. However, because use of a walker usually requires both hands of the patient, a patient is typically unable to take an IV pole with them when using a walker.

Patient care devices and services such as suction and oxygen are not built in to the facilities of several countries and regions. This is also true in field situations of military conflict or civilian disaster. Patients may be far from a medical facility or in the hallway of a medical facility not equipped with patient support equipment/services. Yet a further difficulty exists in maintaining electrical power to electronic devices such as monitoring equipment, suction pumps and/or injection pumps while the patient is walking with an IV pole or walker, or while the patient is being moved in their bed or while the patient is not located next to an electrical outlet. This may occur in: 1) the operating room while needing to adjust the bed height or keep the pumps charged during a long procedure, 2) during a disaster when patients may be stationed in hallways or temporary areas, 3) during military conflict or civilian situations that require creation of field hospitals with limited generator availability, and 4) in countries or regions that do not have consistent access to power. Accordingly, an apparatus that maintains electrical power to these devices would be advantageous, as would an apparatus that provides power in case of an electrical outage or blackout.

In order to move patient support equipment, carts supported by castors are in wide use. Castors may be found in such applications as shopping carts, chairs, hospital beds, and mobile carts. Castors may be fixed or may be capable of swiveling. Typically, remotely operable braking mechanisms used in connection with castors are deployed only on fixed castors. Currently, there is a need for remotely operable braking mechanisms that can be deployed on swiveling castors. More particularly, there is a need for braking mechanisms that can be applied in any rotational position of the castor, and that can be used with castors capable of supporting relatively heavy loads. Additionally, there is a need for control mechanisms that can be used to control a number of castor brakes as well as other cart components.

SUMMARY

The present invention is directed to solving these and other problems and disadvantages or the prior art. Embodiments of the present invention provide a mobile support cart or platform that is structurally stable and can thereby provide weight bearing assistance to a patient without being predisposed to tipping over. A mobile support cart in accordance with embodiments of the present invention includes upper and lower platforms interconnected by first and second support members. The first and second support members and the upper and lower platforms may define a plurality of storage spaces operable to store one or more medical devices that may be needed by a user of the mobile support cart. In addition, the first and second support members and the upper and lower platform may provide a plurality of attachment points. The upper platform may include an ergonomic handle for safe and comfortable user by a patient or other user of the cart.

In accordance with embodiments of the present invention, mobility of the cart is provided by a number of wheels that are disposed on the underside of the lower cart platform. The wheels may include a plurality of castors or castor wheels and a tracking wheel. A braking system may be provided in connection with the castors to brake the cart and/or maintain the cart in a stationary position. Alternatively or in addition, the tracking wheel may be associated with a brake. The tracking wheel may be operable to be lowered and raised between an engaged and a disengaged position. In the engaged position, the tracking wheel is in contact with the underlying support surface (e.g., the floor) on which the mobile support cart moves.

In accordance with embodiments of the present invention, a transmission system is provided that controls the operation of the braking mechanism associated with the castors and the tracking wheel. The transmission system may define a number of modes that establish various degrees of mobility for the cart. In accordance with embodiments of the present invention, three specific modes are defined. In particular, "stop", "walk" and "roll" modes are defined. In the "stop" mode, the castor brakes or braking mechanisms are engaged. In the "walk" mode, the castor brakes are released and the tracking wheel is lowered to its engaged position. In the "roll" mode, the castor brakes are released and the tracking wheel is raised to its disengaged position. In the "stop" mode, the mobile support cart is maintained in a stationary position. In the "walk" mode, the tracking wheel provides guidance or tracking to the movement of the cart. In the "roll" mode, the mobile support cart has its greatest range of motion. In particular, the wheels can rotate or swivel through the 360 degree movement of the castor's bracket or fork.

In accordance with embodiments of the present invention, the control mechanism includes a control arm provided on the underside of the top platform. The arm may include first and second handles that are disposed on the front and rear portions of the top platform. The control arm may include a tracking wheel provided in association with a curved guidance member having a plurality of detents. In particular, pivoting the control arm about a pivot point moves the tracking wheel along an edge of the curved guidance member. Each detent defines a set position for the control arm. These set positions may control the castor wheel brakes and tracking wheel to establish the above described "stop", "walk" and "roll" modes.

In accordance with embodiments of the present invention, the top platform may include recessed portions that provide a means for mounting an oxygen bottle or cylinder onto the cart. Alternatively or in addition, IV receiver pole holes may be associated with the top platform to provide a mounting for IV poles.

Further embodiments of the present invention provide a braking mechanism. Generally, the braking mechanism includes a cable and an associated brake arm, wherein the cable is positioned to allow braking at any point in the castor wheel's 360-degree rotation or swivel. The braking mechanism is associated with a control mechanism that includes a single actuator that operates to separately engage two Bowden cables or two groups of Bowden cables.

In accordance with embodiments of the present invention, a mobile support cart is provided that includes:
- an upper platform;
- a lower platform;
- a vertical member interconnecting the lower platform and the upper platform;
- a plurality of castor wheels interconnected to the lower platform, the castor wheels comprising assemblies, each castor wheel assembly including:
  - a mounting plate, wherein the mounting plate is secured to the lower platform;
  - a bracket, wherein the bracket is rotatably mounted to the mounting plate such that the bracket is free to swivel relative to the mounting plate;
  - a wheel mounted to the bracket;
- a plurality of braking mechanisms, wherein one of the plurality of braking mechanisms is associated with each castor wheel assembly included in the plurality of castor wheel assemblies;
- a tracking wheel assembly, including:
  - a tracking wheel arm, pivotally mounted to the lower platform at a first end;
  - a tracking wheel rotatably mounted to a second end of the tracking wheel arm, wherein the tracking wheel can be placed in either of a lowered position to engage a support surface or a raised position such that the tracking wheel does not engage the support surface;
- a transmission system operable to control the plurality of bracking mechanisms and a position of the tracking wheel, wherein the transmission system can be placed in a selected mode, including:
  - a walk mode, in which the wheels of the castor wheel assemblies are free to rotate and in which the tracking wheel is in the lowered position to engage the support surface;
  - a roll mode, in which the wheels of the castor wheel assemblies are free to rotate and in which the tracking wheel is in the raised position;
  - a stop mode, in which the braking mechanisms are engaged such that the wheels of the castor wheel assemblies are inhibited from rotating and in which the tracking wheel is in the lowered position.

In accordance with other embodiments of the present invention, a castor with a braking mechanism is provided that includes:
- a mounting plate having a central hole formed therein, wherein the central hole is along an axis R;
- a bearing having an open area formed in an area corresponding to an axis of rotation of the bearing;
- a bracket, wherein the bracket is interconnected to the mounting plate by the bearing having an open area formed in an area corresponding to an axis of rotation of the bearing, wherein the axis of rotation of the bearing is parallel to the axis R, and wherein the bracket is capable of swiveling with respect to the mounting plate about the axis of rotation of the bearing;

a wheel interconnected to the bracket;

a brake arm mounted to the bracket by a pivot, the brake arm including:

a first end including a control member attachment point, the first end having a location adjacent the open area formed in an area corresponding to an axis of rotation of the bearing;

a biasing member operable to bias the brake arm in a first direction;

a contact area, wherein the control member one of: 1) allows the biasing member to pivot the brake arm in the first direction such that the contact area engages the wheel, or 2) acts against the biasing member to pivot the brake arm in a second direction opposition the first direction such that the contact area is disengaged from the wheel.

These and other features and advantages of embodiments of the present invention will become more readily apparent from the following description, particularly when taken together with the accompanying drawings.

BRIEF DESCRIPTION OF THE DRAWINGS

FIG. 1 is perspective view of an exemplary mobile cart in accordance with embodiments of the present invention;

FIG. 2 is a side elevation view of the mobile cart shown in FIG. 1;

FIG. 3 is an underside view of the mobile cart shown in FIG. 1;

FIG. 5 is a plan view of an underside portion of the mobile cart shown in FIG. 1, showing a transmission system in accordance with embodiments of the present invention in a first position;

FIG. 6 is another plan view of an underside portion of the mobile cart shown in FIG. 1, showing a transmission system in accordance with embodiments of the present invention in a second position;

FIG. 7 is still another plan view of an underside portion of the mobile cart shown in FIG. 1, showing a transmission system in accordance with embodiments of the present invention in a third position.

FIG. 8 is a front elevation view of a castor, which includes a braking mechanism, in accordance with embodiments of the present invention;

FIG. 9 is a side elevation view of the castor shown in FIG. 8;

FIG. 10 is a perspective view of the castor shown in FIG. 8;

DETAILED DESCRIPTION

Figure 4:
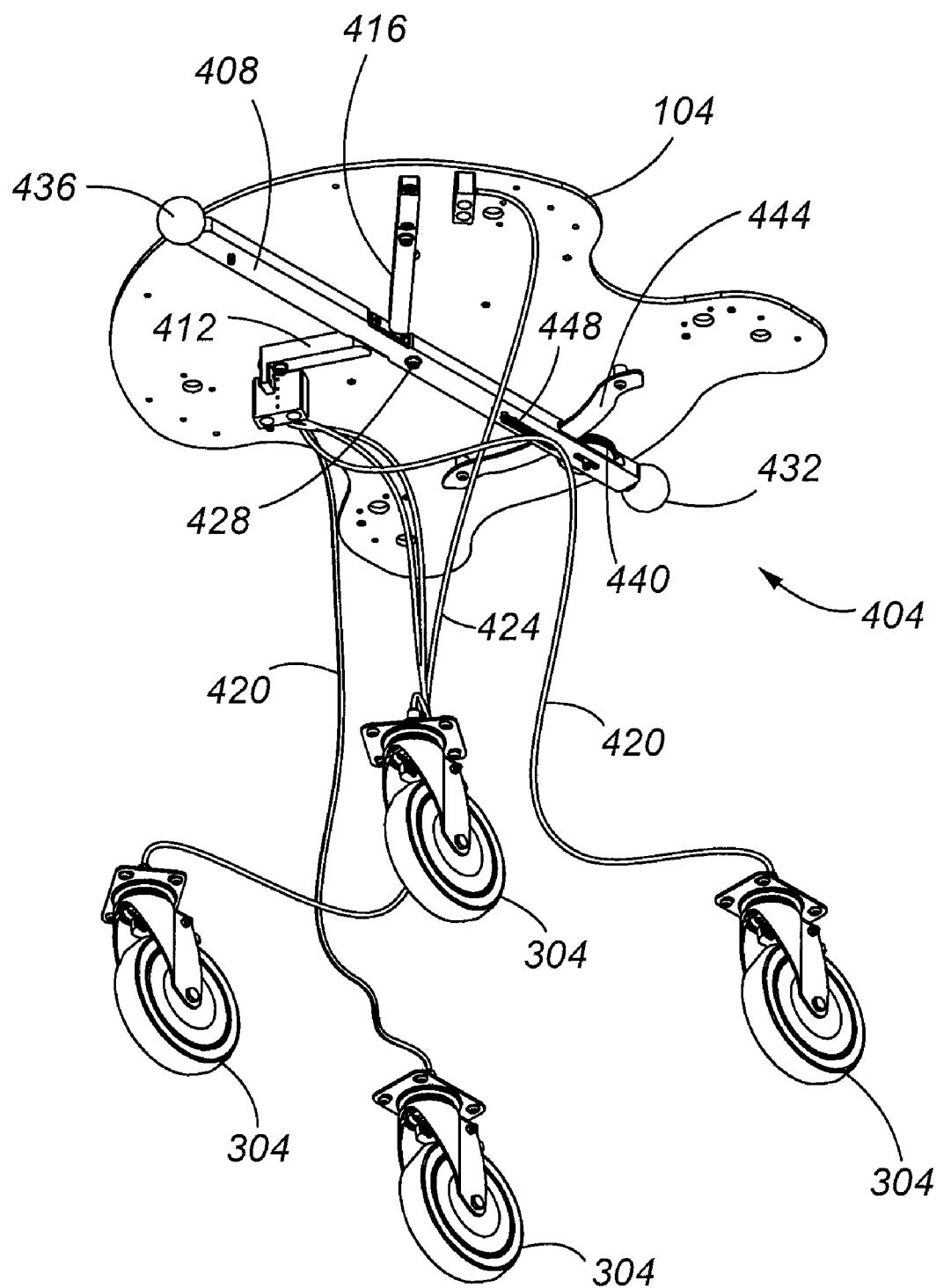
FIG. 4 is a perspective view of a portion of the mobile cart shown in FIG. 1.

The present invention is generally directed to a mobile support cart or platform for use in increasing the mobility of a patient. The present invention is suited for use in a hospital, clinic or other patient care facility. In addition to these environments, the present invention may also be used in other settings such as, for example, a disaster recovery area. A mobile support cart or platform in accordance with embodiments of the present invention provides structure for accommodating a number of medical devices which may be associated with a patient. A mobile support cart, in accordance with embodiments of the present invention, may include a number of selectable modes that define various degrees of mobility for the mobile support cart. In a first mode, an onboard braking system may be engaged that places the mobile support cart in a stopped or braked position by preventing rotation of the castor wheels. In a second mode, the braking system may be disengaged and a tracking wheel may be lowered. In the second mode, the mobile support cart may be guided by the tracking wheel along a user defined path. In a third mode, the braking system is disengaged and the tracking wheel is raised. In this third mode, the patient support platform has its greatest range of motion. More particularly, the castor wheels provided on the base of the mobile support cart are allowed to freely rotate and swivel, thereby providing forward, backward and lateral motion for the mobile support cart.

Referring now to FIG. 1, a mobile support cart in accordance with embodiments of the present invention is generally identified by reference numeral 100. As can be seen in FIG. 1, a mobile support cart 100 in accordance with embodiments of the present invention includes an upper platform 104 and a lower platform 108. The upper platform 104 and the lower platform 108 are interconnected by one or more vertical members, including at least a first support member 112. The upper platform 104 and the lower platform 108 may additionally be interconnected by a second support member 116. The first 112 and second 116 support members may generally include flat, planar surfaces disposed in a substantially vertical orientation. As shown, the second support member 116 may be slightly less wide than the first support member 112. As also shown, the first support member 112 may be split into two separate vertical members or may feature an open area adjacent the lower platform 108. A cover 114 may be associated with one of the vertical members, such as the second support member 116, to assist in the routing of control cables.

As can be seen in the side view of the mobile support cart 100 shown in FIG. 2, the second support member 116 is separated from the first support member 112 by a predetermined distance. The mobile support cart 100 may include a number of storage areas. As seen in FIG. 2, a first storage area 204 is provided between the first 112 and second 116 support members. A second storage area 208 is provided forward of the second support member 116. (As used herein, forward refers to the forward direction of motion of the cart when the cart is pushed or otherwise used for mobility support by a patient.) A third storage area 212 is provided by the top surface of the upper platform 104. A fourth storage area 214 is provided by the top surface of the lower platform 108. These storage areas provide a means for mounting or otherwise carrying medical or other devices that may be needed by the patient. In addition, mounting points may be provided for receiving and/or interconnecting devices to the mobile support cart 100, either directly or through an adapter or container. For example, threaded holes 218 may be provided by the support members 112, 116. A further example are the IV pole receiver holes 128. Such devices may include without limitation IVs and IV poles, IV and entreat pumps, oxygen cylinders, suction wound vacuums, portable ventilators, chest tubes, catheters and drains, ventricular assistant devices, cardiac monitors and defibulators, blood pressure monitors, pulse oxymeters, transesophageal cardiac monitors, tissue oxygenation monitors, invasive cardiac monitors and/or odometers. Plug and play computational devices may be mounted in, for example, the first storage area 204. A wireless communication interface may be provided in connection with the onboard plug and play devices to facilitate transfer of medical data.

An onboard power supply system may be provided for delivering power to one or more of the onboard medical devices. As can be seen in FIGS. 1-2, a mobile support cart 100 in accordance with embodiments of the present invention includes a power outlet box 120 disposed on a rear portion of the mobile support car 100. More particularly, the power outlet box 120 may be mounted underneath the upper platform 104 and on a rear facing side of the first support member 112. (As used herein, rear or rearward refers to the reverse direction of motion of the cart when the cart is pulled by a patient.) Electrical power may supplied from a wall outlet or other source through a power cord 216. The power cord 216 may be extendable and retractable with respect to the power outlet box 120. Alternatively or in combination, the power outlet box 120 may be provided in association with an onboard power source or universal power supply 220. As shown in FIG. 2, the universal power supply 220 may be mounted or otherwise located on the lower platform 108. The universal power supply 220 is mounted in this position to provide added stability to the mobile support cart 100. In particular, as the universal power supply 220 provides substantial weight to the cart, the universal power supply 220 is provided close to the base of the cart, thereby lowering the center of gravity of the cart. Examples of a universal power supply 220 include an isolation transformer, a battery, and/or a fuel cell.

Referring again to FIG. 1, a number of features are illustrated herein that facilitate attachment of onboard equipment. As can be seen in FIG. 1, the mobile support cart 100 includes an attached IV pole 124. The attached IV pole 124 is mounted to the mobile support cart 100 through an IV pole receiver hole 128, which is disposed on the surface of the upper platform 104. The mobile support cart 100 shown in FIG. 1 includes two IV pole receivers 128. It should be understood however, that a number of IV pole receiver holes may be associated with a particular mobile support cart 100.

The upper platform 104 may additionally include two recessed side cut portions 132. The recessed side cut portions 132 are adapted to receive a cylindrical object such as an oxygen tank or bottle. In particular, the oxygen tank or bottle may be placed on the surface of the lower platform 108, in a position where the upper end of the cylinder or bottle is cradled at its upper end by the recessed side cut portion 132 of the upper platform 104. The cylinder or bottle may then be secured in place by a fastener member, which attaches to one or both of the support members 112 and 116 to thereby immobilize the cylinder or bottle.

As can be seen in FIGS. 1 and 2, a mobile support cart 100 in accordance with embodiments of the present invention includes a platform handle 136. The platform handle 136 may be of an ergonomic design adapted specifically for patient comfort and safety. The platform handle 136 is disposed approximately at lower to mid chest level and includes two raised hand gripping portions 140. The platform handle 136 provides for a symmetric axial loading of the patient's arms. In this regard, the platform handle 136 transfers the force associated with moving the mobile support cart 100 to the scapula and/or to the back and not to the sternum of the patient or user. The platform handle 136 also allows the quadriceps to participate in the pushing of the mobile support cart. In using the platform handle 136, the patient's joints are at a midpoint in their range of motion. Generally, the design of the mobile support cart 100, including the platform handle 136, is adapted to resist rotational movement, thereby preventing excessive strain on the patient and the patient's limbs. The above described advantages are in contrast with the standard mobile IV pole known in the art. In moving a standard IV pole, a patient must rely exclusively on the pectoralis and smaller muscle groups to move the pole. This creates leverage on the sternum and a twisting strain on the torso. Moreover, the patient's joints are extended beyond the midpoints of their ranges of motion, thereby increasing strain on the joints. Moreover still, prior art mobile IV poles are prone to twisting and catching on surfaces, thereby exposing the patient to greater risk of injury.

As can be seen in FIGS. 1 and 2, a number of castors 304 provide mobility for the mobile support cart 100. The castors 304 are better seen in FIG. 3, which shows an underside of the mobile support cart 100. In accordance with embodiments of the present invention, the mobile support cart 100 includes a plurality of castors 304 or means for traversing an underlying or supporting surface. Additionally, the mobile support cart 100 includes a tracking wheel 308 or means for providing tracked movement. As can be seen in FIG. 3, two castors 304 are mounted on a front or forward portion of the lower platform 108. Two of the castors 304 are mounted on a rearward portion of the lower platform 108. The tracking wheel 308 is mounted in or near the center of the lower platform 108. FIG. 2 shows a profile of the mobile support cart, including components associated with the tracking wheel 308. As shown therein, the tracking wheel 308 is part of an assembly that includes a tracking wheel arm 224. The tracking wheel arm 224 is mounted at an attachment point 228 that is disposed at the forward end of the lower platform 108. The tracking wheel arm 224 is additionally associated with a biasing spring 232. The biasing spring 232 operates to bias the lever arm 224 in a downward position, wherein the tracking wheel 308 is engaged with the underlying surface.

The mobile support cart 100 may include a transmission or transmission system having a lift cable that is operable to lift the tracking wheel 308 and tracking wheel arm 224 against the action of the biasing spring 238. In the raised position, the tracking wheel 308 is disengaged from the underlying surface. FIG. 4 provides an illustration of components that may be included in a transmission system 404 in accordance with embodiments of the present invention. FIG. 4 shows an underside of the top platform 104 including connections to other cart components. Particular portions of the mobile support cart 100 are omitted from FIG. 4 to simplify the illustration. The transmission system 404 includes a control arm 408 that can be moved into at least two and preferably three positions to select from two or three modes of operation. The control arm 408 is operatively associated with a first or short lever 412 and a second or long lever 416. The short lever 412 is interconnected to one or more brake cables 420. The long lever 416 is interconnected to a lift cable 424 or means for raising and lowering the tracking wheel 308. The brake cables 420 and/or the lift cable 424 may comprise Bowden cables or the like and are operatively associated with the castors 304 and the tracking wheel 308, respectively. The lift cable 424 that is associated with the long lever 416, is used to lift or otherwise control a different cart component than those controlled by the brake cable(s) 420. For example, the lift cable 424 may be used to control whether the tracking wheel 308 is in a retracted position in which the tracking wheel 308 is disengaged from the floor or support surface, or is in a lowered position in which the tracking wheel is engaged with the floor or support surface. Alternatively, the lift cable 424 may be used to actuate other cart components such as a transmission, a gear system, or additional braking mechanisms.

In moving the short lever 412 and the long lever 416, the control arm 408 includes an attachment point that provides a rotatable connection to the upper platform 104. In particular, a pivot type connection 428 is provided at or near the center of the underside of the upper platform 104. The control arm 408 is adapted to move or pivot about the attachment point 428. The control arm 408 may include a first 432 and second 436 handle that may be gripped by a user to rotate the arm 408. The first or rear handle 432 may be provided at the rear of the control arm 408. The rear handle 432 is typically operated by a patient who is using the mobile support cart 100 to enhance his or her mobility. The second or forward control handle 436 may be provided at the forward end of the control arm 408. Typically, this forward control handle 436 is used by doctors, nurses or other hospital staff in moving or controlling the mobile support cart 100 or in demonstrating the various modes of the cart to a patient who is typically located at the rear of the mobile support cart 100.

In accordance with embodiments of the present invention, the control arm 408 includes a guide wheel 440 provided in association with a curved guidance member 444. The guide wheel 440 is biased by a guidance wheel spring 448 that maintains the guide wheel 440 in operative contact with the curved guidance member 444. The guide wheel 440 is mounted to the control arm 408. For example, the guide wheel 440 may be mounted within a slot 452 formed in the control arm 408. The curved guidance member 444 is disposed so that it is in contact with the guide wheel 440. For instance, the curved guidance member 444 may be disposed in the slot 452 in the control arm and may be mounted on the underside of the upper platform 104. As the control arm 408 is rotated about the attachment point 428, the guidance wheel 440 moves along an edge 442 of the curved guidance member 444. A number of discrete set positions are defined for the rotatable arm 408 by a number of detents 504 (see FIGS. 5-7) associated with the forward edge 442 of the curved guidance member 444. In particular, as the control arm 404 is moved such that the guide wheel 440 reaches a defined control position, the guide wheel 440 is drawn into the particular detent 504 to provide a set point for the control arm 408. More particularly, the guide wheel 440 is biased by a guide wheel spring 448. As a result, a force is required to dislodge the guide wheel 440 from a detent 504 in the curved guide member edge 444. In this way, a number of tangible set positions is established for the control arm 408. Moreover, because any one of these operating modes provided by the mobile supply cart can be selected using the control arm 408, the control arm 408 is part of a single selection mechanism that can also include the guidance wheel 440, guidance member 444, the short lever 412, the long lever 416, The Bowden cables 420, 424 and other associated components.

In embodiments of the present invention that include a tracking wheel 308, the mobile support cart 100 may include three modes. In a "stop" mode, the mobile support cart 100 is prevented from moving freely. In a "walk" mode, the mobile support cart 100 is allowed to move, but the tracking wheel 308 prevents or inhibits lateral movement, to provide guided or tracked movement. In a "roll" mode, the mobile support cart 100 is allowed to move freely. As shown in FIGS. 5-7, first, second and third detents 504a-c may be associated with the curved guidance member 444 to provide three set points for the control arm 408 that set the mobile support cart 100 in the three modes. These three modes are described in connection with FIGS. 5-7, which each show one of the three positions of the transmission system 404.

In FIG. 5, the control arm 408 has been moved into a position that engages the short lever 412 such that the short lever 412 has been moved from the short lever's first position to the short lever's second position and leaves the long lever 416 in the long lever's first position. Here, the cart is in a "stop" mode. In particular, as the short lever 412 rotates, it retracts and applies a tensile force to the inner cable of the brake cables 420. This causes a braking mechanism associated with each castor 304 to engage. Additionally, in the "stop" mode the tracking wheel 308 is not retracted. In the "stop" mode the guidance wheel 440 is located in the first detent 504a.

In FIG. 6, the control arm 408 is moved into a neutral position that leaves both the short lever 412 and the long lever 416 unaffected such that they are in the first or vertical positions to which they are normally biased. Here, the cart is in a "walk" mode. In particular, the braking mechanisms associated with the castors 304 are not engaged and the tracking wheel 308 is not retracted. Accordingly, the tracking wheel 308 is engaged with the floor or underlying surface under the action of the spring 232. In this position, the tracking wheel 308 operates to provide tracked movement of the mobile support cart 100. In the "walk" mode the guidance wheel 440 is located in the second detent 504b.

In FIG. 7, the control arm 408 is moved into a position that engages the long lever 416 such that the long lever is moved to a second position of that lever and leaves the short lever 412 in the first position of that lever. Here, the cart is in a "roll" mode. In particular, as the long lever 416 rotates, it applies tension to and retracts the lift cable 424. This causes the tracking wheel 308 to be retracted against the action of the spring 232 such that the tracking wheel is lifted and is disengaged from the support surface or floor. With the tracking wheel 308 disengaged from the floor, the mobile support cart 100 is allowed to roll freely. In the "roll" mode the guidance wheel 440 is located in the third detent 504c.

FIGS. 8-10 illustrate an exemplary castor wheel 304 assembly 812 that includes a braking mechanism 804 in accordance with embodiments of the present invention. The braking mechanism 804 is used to brake an associated castor wheel 812 in such a way that the castor 812 maintains the freedom to swivel 360 degrees. The castor wheel assembly 812 includes a wheel 306 mounted to a bracket or fork 816. The wheel 304 together with the bracket 816 is interconnected to a mounting plate 820 by a swivel or bearing to allow the wheel 304 and bracket 316 to swivel. The braking mechanism 804 features a brake cable 420 operatively associated with a brake arm 824. The brake cable 420 may comprise a Bowden cable having a flexible inner cable within a hollow outer housing. The brake cable 420 passes through a central hole located in the mounting plate 820 and through an open area formed in an area corresponding to and encompassing an axis of rotation of the bearing. The mounting plate 820 may include a plurality of mounting points 822 (see FIG. 10), and an area generally between at least some of the plurality of mounting points 822 defines an area through which the axis of rotation R passes. In accordance with embodiments of the present invention, the mounting points 822 comprise holes through which fasteners may be received or passed through the mounting plate 820. The brake arm 824 is pivotally mounted to the bracket 816. A biasing member such as a spring 828 normally biases the brake arm 824 to a position disengaged from the castor wheel 304. A user may engage the braking mechanism 804 by actuating an associated control mechanism, such as the transmission system 404, which is disclosed herein. Alternatively, the braking mechanism 804 may be controlled by other control mechanisms or actuators, such as a handgrip lever brake. An actuation of the associated control mechanism places the inner cable of the brake cable in tension and causes the inner cable of the brake cable 420 to retract such that the end of the brake arm 824 to which the inner cable is attached is drawn towards the mounting plate 820. The inner cable acts against the bias of the spring 828 causing the end of the brake arm 824 opposite the end attached to the inner cable to pivot into engagement with the wheel 306. The inner cable of the brake cable 420 passes through the mounting plate 820 along an axis R, about which the wheel 306 and bracket 816 swivels. This orientation of the brake cable 420 allows the braking mechanism 804 to engage at any point in the 360-degree swivel motion of the wheel 306 and bracket 816 around the axis R. In addition, the freedom of the wheel 308 and the bracket 816 to swivel relative to the mounting plate 820 is not inhibited or limited by the braking mechanism 804.

Figure 11:
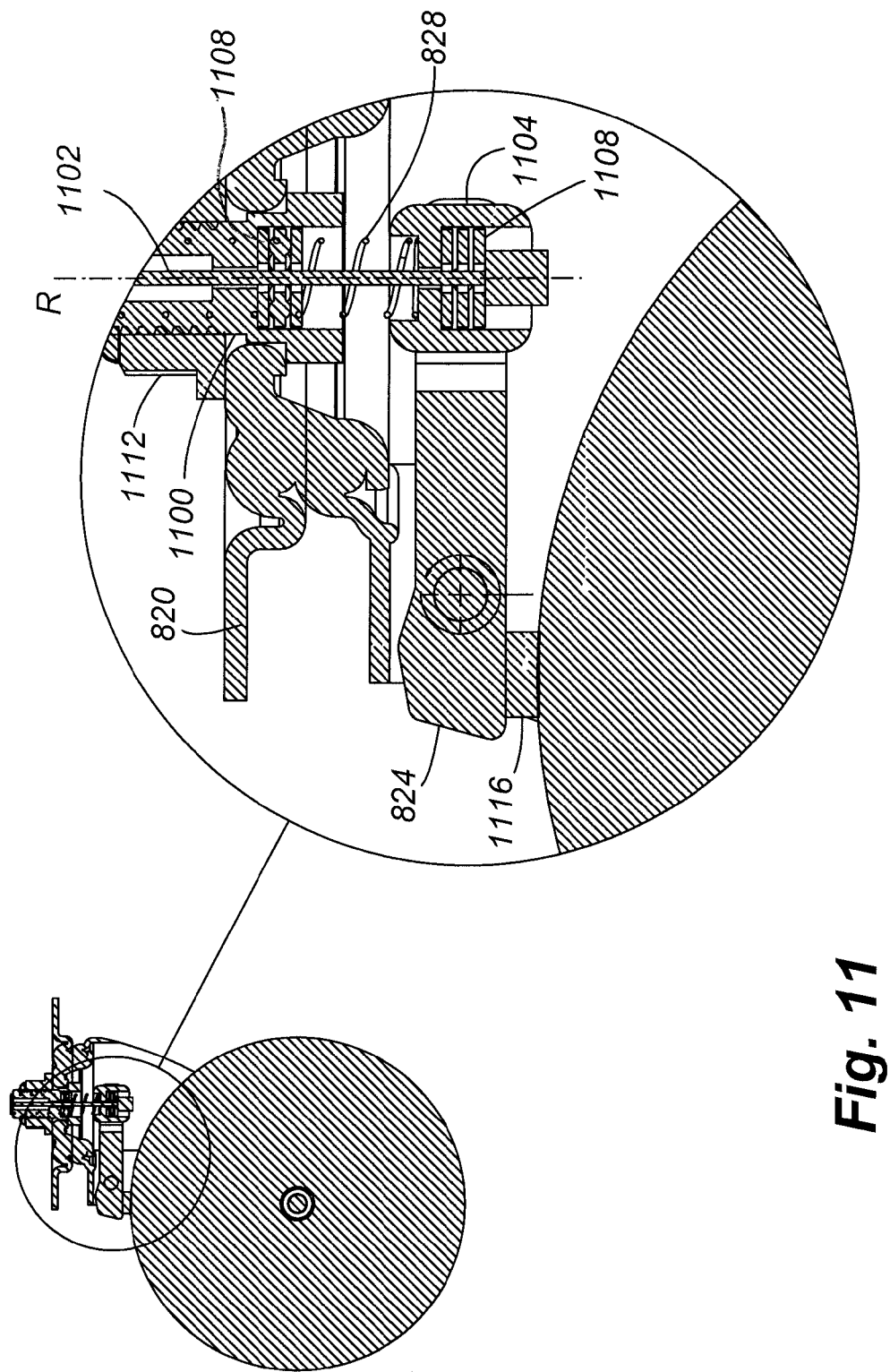
FIG. 11 is an enlarged view of a braking mechanism, in accordance with embodiments of the present invention.

FIG. 11 is an enlarged view of a braking mechanism 804, in accordance with embodiments of the present invention. The braking mechanism 804, shown in FIG. 11 includes an insert member or ferrule 1100 that operates to maintain the alignment of the brake cable 420. In particular, the portion of the brake cable 420 that passes through the mounting plate 820 is maintained in alignment with the axis of rotation R of the castor wheel 304 and bracket 816. More particularly, the location of the end of the brake cable 420 housing remains fixed with respect to the plate 824, as the castor wheel 304 and bracket 816 rotates with respect to the mounting plate 820. The brake arm 824 is interconnected to the inner cable 1102 of the brake cable 420 through a swivel 1104 that allows the brake arm 824 to rotate with respect to the brake cable 420. Both the insert member 1100 and the swivel 1104 may include a thrust bearing 1108 that facilitates the interconnection of the brake cable 420 to the castor 812. The insert member 1100 may be held in place by a retention nut 1112. A contact area or brake pad 1116 may be disposed on the end of the brake arm 824 for engagement with the castor wheel 304. In accordance with embodiments of the present invention, the brake pad 1116 comprises a rubber stop. A castor wheel assembly 812 may be manufactured with the various parts described in connection with FIG. 11, including the insert member 1100, the swivel 1104 and the brake arm 824. Alternatively, one or more of these parts may be machined for incorporation with an existing plate castor.

Figure 12:
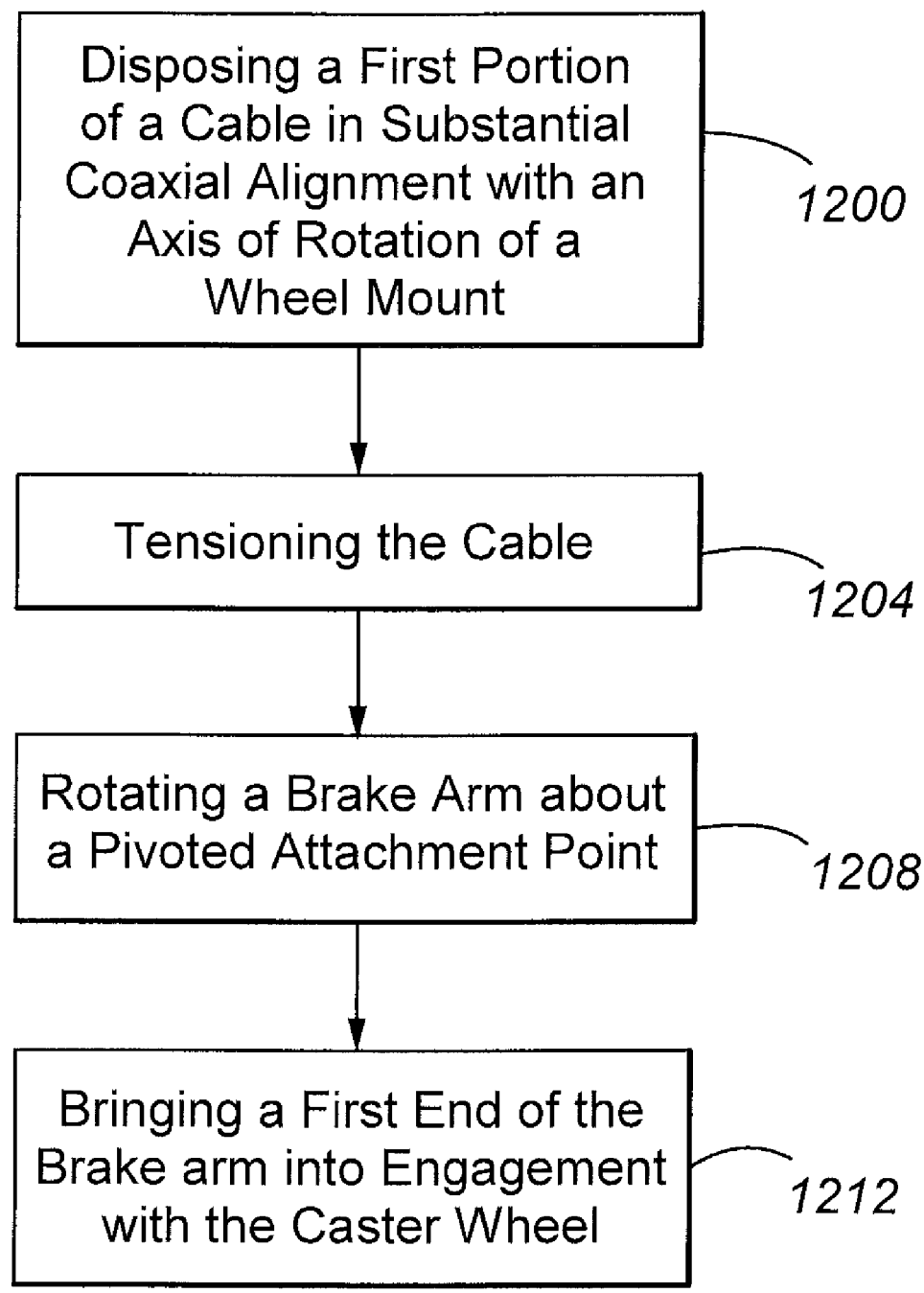
FIG. 12 is a flow chart showing a method of braking a castor in accordance with embodiments of the present invention.

FIG. 12 is a flow chart showing the steps in a method of braking a castor, in accordance with embodiments of the present invention. Initially, at step 1200 a first portion of a brake cable 420 is disposed in a substantial coaxial alignment with an axis R about which a wheel mount or bracket 820 swivels. At step 1204, the brake cable 420 is tensioned. At step 1208, as a result of the tensioning the brake cable 420, a brake arm 824 is rotated about a pivoted attachment point. At step 1212, as a result of the rotation of the brake arm 824, an end of the brake arm 824 is brought into engagement with the wheel 306, to thereby brake to wheel 306.

Figure 13:
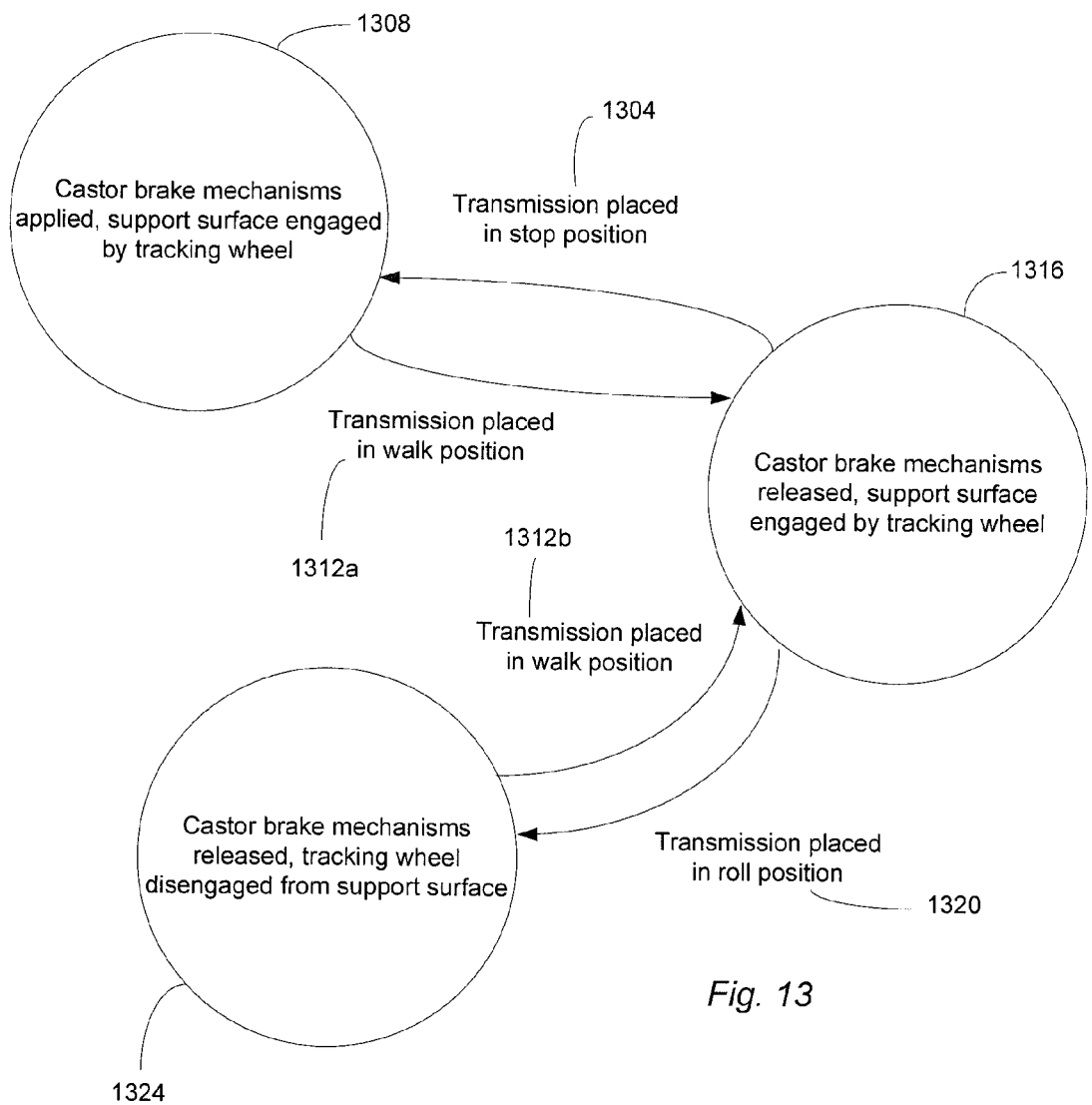
FIG. 13 is a state diagram depicting the various states of a mobile support cart in accordance with embodiments of the present invention.

FIG. 13 is a state diagram depicting the different states in which a mobile support cart 100 having a transmission system 404 in accordance with embodiments of the present invention can be placed. When the transmission system 404 is placed in a "stop" position 1304, the mobile support cart 100 is in the "stop" mode 1308, with the castor brake mechanisms or braking mechanisms 804 applied, and with the support surface or floor engaged by the tracking wheel 308. In accordance with embodiments of the present invention, the transmission system 404 is placed in the "stop" position by moving a handle 432 or 436 of the control arm 408 into a position marked on the upper surface of the upper platform 104 as corresponding to the stop mode.

In accordance with embodiments of the present invention, the transmission system 404 can be moved from the "stop" mode 1308 to a "walk" mode 1316 by moving the control arm 408 from the "stop" position to the "walk" position. In the "walk" mode 1316, the castor brake mechanisms 804 are released, and the support surface or floor is engaged by the tracking wheel 306.

From the "walk" mode 1316, the transmission system 404 can be placed in a roll position 1320. Placing the transmission system 404 in the "roll" position 1320 can include moving a handle 432 or 436 of the control arm 408 to a position marked on the top surface of the upper platform 104 as corresponding to the "roll" mode 1324. In the "roll" mode 1324, the braking mechanisms 804 are released, and the tracking wheel 306 is disengaged from the support surface.

In accordance with embodiments of the present invention, from the "roll" mode 1324, the transmission system 404 can be placed back into the "walk" position 1312b, to place the mobile support cart 100 in the "walk" mode 1316. Therefore, it can be appreciated that at least some embodiments of a mobile support cart 100 in accordance with the present invention require that the "walk" mode 1316 be entered, at least momentarily, when switching from any of the other modes 1308 or 1324. However, other embodiments of the present invention are not limited in this way.

Although particular examples and embodiments of a mobile support cart 100 in accordance with embodiments of the present invention have been described herein, variations of the mobile support cart 100 are possible, and are within the scope of the present invention. For example, the transmission system 404 is not necessarily limited to an arrangement comprising short and long arms 412, 416 and cable actuated control of the braking mechanisms 804 and of the tracking wheel 308. For example, push rods and/or screw type members may be used to transfer control inputs from a control arm 408 to the braking mechanisms 804 and/or the tracking wheel 308. In addition, although certain exemplary embodiments have featured braking assemblies 804 that are biased towards a disengaged position, other embodiments of the present invention may incorporate braking mechanisms 804 that are biased towards an engaged position. According to such embodiments, in a "walk" 1316 or "roll" 1324 mode, the transmission system 404 would be operated to act against the bias, while in the "stop" mode 1308 the transmission system 404 would be operated to release the braking mechanisms 804 such that the biasing member was free to place the contact area or brake pad into contact with the castor wheels 304. The position of the tracking wheel 308 may, according to embodiments of the present invention, be biased towards a raised position, although biasing the tracking wheel 308 towards a lowered or engaged position can be advantageous where the support surface is uneven. As yet another variation, embodiments of the present invention may feature a control arm 408 that is turned or rotated by a user to select the desired mode 1308, 1316 or 1324. According to such embodiments, the control arm 408 may be associated with cams or lifters to control the positions of the braking mechanisms 804 and the tracking wheel 306.

The foregoing discussion of the invention has been presented for purposes of illustration and description. Further, the description is not intended to limit the invention to the form disclosed herein. Consequently, variations and modifications commensurate with the above teachings within the skill or knowledge of the relevant art are within the scope of the present invention. The embodiments described herein above are further intended to explain the best mode presently known of practicing the invention and to enable others skilled in the art to utilize the invention in such or in other embodiments and with various modifications required by the particular application or use of the invention. It is intended that the appended claims be construed to include alternative embodiments to the extent permitted by the prior art.

What is claimed is:

1. A support cart for traversing an underlying surface, comprising:
    a frame;
    a plurality of castor wheels interconnected to the frame;
    a braking mechanism interconnected to at least one of the castor wheels, wherein the braking mechanism includes:
        a wheel mount interconnected to the support cart;
        a plate member interconnected to the wheel mount, the plate member including a swiveled attachment to the wheel mount and at least a first hole aligned with an axis of rotation of the wheel mount, wherein the plate member includes a plurality of mounting points, at least some of the plurality of mounting points defining an area through which the axis of rotation passes;
        a brake arm pivotally connected to the wheel mount, the brake arm having a first end and a second end, the first end adapted for engaging a wheel carried by the wheel mount, the first end including a contact area;
        a spring disposed between the second end of the brake arm and the plate member, the spring causing the brake arm to be normally in a position wherein the first end of the brake arm is disengaged from the castor wheel;
        a brake cable having a first end and a second end, the first end connected to the second end of the brake arm, the first end having a first portion extending from the second end of the brake arm through the first hole in the plate member, the first portion of the brake cable being substantially aligned with the axis of rotation of the wheel mount;
        wherein a tensioning of the cable causes the brake arm to pivot, causing the contact area at the first end of the brake arm to engage the castor wheel, causing a braking action on the castor wheel; and
    a transmission system interconnected to said frame, the transmission system providing a number of user selectable modes, the user selectable modes comprising at least a stop mode, and a roll mode, wherein in the stop mode each braking mechanism is engaged, and in the roll mode each braking mechanism is disengaged.

2. The support cart of claim 1, further comprising:
    a plurality of braking mechanisms;
    a single selector mechanism for selectively choosing at least the stop and roll modes;
    wherein the single selection mechanism includes a control arm associated with a short lever and a long lever, the short lever being interconnected to a plurality of brake cables, wherein each one of the plurality of brake cables is associated with one of the braking mechanisms, and the long lever being interconnected to a lift cable, the control arm being movable between three positions, wherein:
    in a first position, the short lever is engaged and the long lever is not engaged, wherein engaging the short lever causes a tensioning of each brake cable which causes a engagement of each braking mechanism;
    in a second position, the short lever is not engaged and the long lever is not engaged; and
    in a third position, the short lever is not engaged and the long lever is engaged, wherein engaging the short lever causes a tensioning of a lift cable interconnected to a tracking wheel.

3. The support cart of claim 2, wherein the control arm includes a guide wheel provided in association with a curved guidance member having a number of detents disposed along an edge thereof, wherein the first, second and third positions are defined by an engagement of the guide wheel with a particular detent.

4. The support cart of claim 2, wherein the control arm includes a first handle at a rear portion of said frame and a second handle at a front portion of said frame, said first and second handle for selectively adjusting a setting of the transmission system.

5. The support cart of claim 1, wherein the frame includes an upper platform and a lower platform.

6. The support cart of claim 5, further comprising:
    a power supply provided in association with a power outlet box, the power supply being mounted on the lower platform and the power outlet box being connected to the frame proximate to the upper platform.

7. The support cart of claim 5, wherein the upper platform includes a recessed side cut adapted to cradle an upper portion of a cylindrical object when the cylindrical object is placed on the lower platform.

8. The support cart of claim 5, wherein the upper platform includes an IV pole receiver hole.

9. The support of cart of claim 5, wherein the upper platform and the lower platform are interconnected by first and second planar support members, the first and second planar support members defining a plurality of storage spaces.

10. The support cart of claim 1, further comprising:
    a power supply interconnected to the frame.

11. The support cart of claim 1, wherein the braking mechanism further includes:
    an insert member disposed between the brake cable and the plate member, the insert member being operable to maintain the alignment of the brake cable.

12. A method of controlling a personal support cart, comprising:
    moving a single selector mechanism into a first position to thereby place the support cart in a stop mode, wherein in the stop mode a plurality of braking mechanisms are engaged;
    moving the single selector mechanism into a second position to thereby place the support cart in a roll mode, wherein in the roll mode the braking mechanisms are disengaged;
    wherein each of the braking mechanisms is connected to a castor wheel, wherein engaging the braking mechanisms includes, for each braking mechanism:
        tensioning a cable, a first portion of the cable being disposed in substantial coaxial alignment with an axis of rotation of a wheel mount, the wheel mount having a swiveled attachment to a plate member adapted for connecting the castor wheel to the personal support cart, the plate member having at least a first hole aligned with the axis of rotation of the wheel mount, and wherein the first portion of the cable extends through the first hole in the plate member to a brake arm, the cable being interconnected to the brake arm, the brake arm having a first end and a second end, the first end being adapted for engagement with the castor wheel, the cable being attached to the second end;

as a result of the tensioning of the cable, rotating the brake arm about a pivoted attachment to the wheel mount; and as a result of rotating the brake arm, bringing the first end of the brake arm into engagement with the castor wheel causing a braking action on the castor wheel, wherein the single selector mechanism includes a control arm associated with a short lever and a long lever, the short lever being interconnected to a plurality of brake cables and the long lever being interconnected to a lift cable, the control arm being movable between three positions, wherein in a first control arm position, the short lever is engaged and the long lever is not engaged, wherein engaging the short lever causes a tensioning of each brake cable which causes a engagement of each braking mechanism;

in a second control arm position, the short lever is not engaged and the long lever is not engaged; and in a third control arm position, the short lever is not engaged and the long lever is engaged, wherein engaging the short lever causes a tensioning of the lift cable.

13. The method of claim 12, wherein the control arm includes a guide wheel provided in association with a curved guidance member having a number of detents disposed along an edge thereof, wherein the first position, the second position and the third positions are defined by an engagement of the guide wheel with a particular detent.

14. The method of claim 12, further comprising:

setting the control arm in the first, second and third positions using at least one of a first handle included in the control arm at a rear portion of said frame and a second handle included in the control arm at a front portion of said frame.

* * * * *